(12) United States Patent
Lehtonen et al.

(10) Patent No.: US 9,394,207 B2
(45) Date of Patent: Jul. 19, 2016

(54) FERTILIZER, ITS USE AND A PROCESS FOR PREPARING IT

(71) Applicant: BIOKASVU OY, Tarvasjoki (FI)

(72) Inventors: Keijo Lehtonen, Marttila (FI); Juha Tilkanen, Kyrö (FI)

(73) Assignee: Biokasvu Oy, Tarvasjoki (FI)

( * ) Notice: Subject to any disclaimer, the term of this patent is extended or adjusted under 35 U.S.C. 154(b) by 0 days.

(21) Appl. No.: 14/381,250

(22) PCT Filed: Feb. 27, 2013

(86) PCT No.: PCT/FI2013/050223
§ 371 (c)(1),
(2) Date: Aug. 27, 2014

(87) PCT Pub. No.: WO2013/128080
PCT Pub. Date: Sep. 6, 2013

(65) Prior Publication Data
US 2015/0101376 A1    Apr. 16, 2015

(30) Foreign Application Priority Data

Feb. 28, 2012 (FI) ..................................... 20125220

(51) Int. Cl.

| | | |
|---|---|---|
| C05C 1/00 | (2006.01) | |
| C05C 9/00 | (2006.01) | |
| C05C 11/00 | (2006.01) | |
| C05B 15/00 | (2006.01) | |
| C05B 17/00 | (2006.01) | |
| C05C 3/00 | (2006.01) | |
| C05F 17/00 | (2006.01) | |
| C05G 1/00 | (2006.01) | |
| A01C 21/00 | (2006.01) | |
| A01N 25/12 | (2006.01) | |
| C05G 3/00 | (2006.01) | |

(52) U.S. Cl.
CPC ................. *C05B 17/00* (2013.01); *A01C 21/00* (2013.01); *A01N 25/12* (2013.01); *C05C 3/00* (2013.01); *C05C 11/00* (2013.01); *C05F 17/0045* (2013.01); *C05G 1/00* (2013.01); *C05G 3/00* (2013.01); *C05G 3/0058* (2013.01); *C05B 15/00* (2013.01); *C05C 1/00* (2013.01); *C05C 9/00* (2013.01); *Y02E 50/343* (2013.01); *Y02P 20/145* (2015.11); *Y02W 30/43* (2015.05); *Y02W 30/47* (2015.05)

(58) Field of Classification Search
None
See application file for complete search history.

(56) References Cited

U.S. PATENT DOCUMENTS

| | | | | |
|---|---|---|---|---|
| 1,368,249 | A * | 2/1921 | Ducommon | ............ C05B 17/00 435/252.1 |
| 2,117,087 | A | 5/1938 | Formhals | |
| 2,612,497 | A * | 9/1952 | Meijer | ................... C07H 13/12 536/29.12 |
| 3,878,304 | A * | 4/1975 | Moore | ..................... A23K 1/22 426/635 |
| 4,251,255 | A * | 2/1981 | Wagner | ................... C05C 11/00 504/101 |
| 4,283,219 | A * | 8/1981 | Wagner | ................... C05C 11/00 504/245 |
| 4,333,757 | A * | 6/1982 | Kurtzman, Jr. | .......... A01G 1/04 47/1.1 |
| 4,839,088 | A * | 6/1989 | Young | .................... A01N 59/02 127/29 |
| 5,114,458 | A * | 5/1992 | Castillo | ................ C05G 3/0088 71/28 |
| 5,328,497 | A * | 7/1994 | Hazlett | ................ C05G 3/0088 71/26 |
| 5,549,729 | A | 8/1996 | Yamashita | |
| 2004/0200248 | A1 | 10/2004 | Kirkegaard | |
| 2011/0072872 | A1* | 3/2011 | Hartle | ........................ C05B 7/00 71/27 |
| 2012/0011910 | A1 | 1/2012 | Daniels | |
| 2013/0125598 | A1* | 5/2013 | Bradbury | ................ C05B 17/00 71/17 |
| 2014/0345342 | A1* | 11/2014 | Ushijima | ................... B01J 2/30 71/11 |

FOREIGN PATENT DOCUMENTS

| | | |
|---|---|---|
| AU | 2007209830 | 3/2008 |
| CA | 2100017 | 7/1993 |
| CN | 1210843 | 3/1999 |
| WO | 9117130 A1 | 11/1991 |
| WO | 9706121 A1 | 2/1997 |

OTHER PUBLICATIONS

National Board of Patents and Registration of Finland. Search Report dated on Nov. 13, 2012.
PCT International Search Report of Jun. 13, 2013.
PCT Written Opinion of Mar. 17, 2014.

* cited by examiner

*Primary Examiner* — Wayne Langel
(74) *Attorney, Agent, or Firm* — Berggren Inc.

(57) ABSTRACT

The invention relates to fertilizer compositions comprising a carbon source and a source of nitrogen. Carbon is in form that can be readily up-taken by soil bacteria. The invention also relates to a method for manufacturing the fertilizer, a method for fertilizing soil and uses of said fertilizer. Use of the fertilizer promotes uptake of endogenous soil nutrient resources by plant.

16 Claims, No Drawings

FERTILIZER, ITS USE AND A PROCESS FOR PREPARING IT

CLAIM OF PRIOITY

This application is a national application of international application number PCT/FI2013/050223 filed on Feb. 27, 2013, which claims priority of national Finnish patent application number FI20125220 filed on Feb. 28, 2012, both of which are incorporated herein by reference in their entirety.

FIELD OF INVENTION

This invention relates to fertilizer compositions comprising a mixture of at least carbon and nitrogen. Further the invention relates to a method for fertilizing soil and a method of manufacturing said fertilizer. Also uses of the fertilizers are disclosed.

DESCRIPTION OF RELATED ART

Agricultural plant production has for long times based on industrial plant fertilizers, even to such extent, that e.g. in Finland agricultural soil has become enriched in nitrogen 100000 t/y (47 kg nitrogen/ha/y). This nitrogen has participated as a nutrient in the microbiological degradation of the soil organic matter and humus biosynthesis, and has in large extent become part of soil humus resources. In recent years the needs for natural resources have become stronger, and as a consequence e.g. natural phosphorus resources have been estimated to finish in few decades. Industrial production of nitrogen fertilizers, on the other hand, uses enormous amounts of natural resources and energy. Fertilizer raw-material prices have strongly risen, and will already threaten, besides the income of agricultural producers but also the increasing number of consumers as more expensive prices for foodstuffs.

It is a known fact, that addition of glucose into soil activates soil bacteria to degrade soil organic matter in a process called priming effects. Priming effects have been found to depend on the microbial carbon content of the soil: priming effect (as $CO_2$—C, µg/g soil) vs. easily-available substrate carbon added to the soil/microbial carbon content of the organic carbon content of the soil (% by weight). This dependence of glucose induced priming effects is linear to 15% by weight (of added priming carbon in relation to microbial carbon), and after 50% by weight an exponential decrease or even a switch to negative priming effect is often observed at about 500 to 600% by weight. It is also known, that nitrogen compounds, e.g. amino acids or fertilizer nitrogen, at low levels strengthen the priming effects. Soil bacteria need two energy carbons for cell respiration to bind one carbon into their cell structure. Soil bacteria bind carbon and nitrogen in their cell structure in the carbon/nitrogen ratio 5:1-6:1. Nutrients from the turnover of soil bacteria will become available plant nutrients.

JP9100189 discloses a fertilizer containing sugar and saccharide. The fertilizer has a compounding ratio from 5 to 6% dry microbial cell fertilizer, 30 to 40% corn jam meal and from 50 to 60% general fertilizer. Said sugar containing fertilizer proposed to stimulate growth of the microorganism and improve the dispersion of the fertilizer and quality of crops.

CA2100017 discloses a slow release fertilizer encapsulated in a hydrophilic polysaccharide. The ratio of nitrogen source to sugar is between about 1:1 to about 20:1 on dry matter basis.

WO 97/06121 discloses a slow release organic fertilizer which is composed of 50 to 95% by weight of manure and 5 to 50% by weight clay filter material. Clay filter material contains 5 to 50% by weight of residual oil.

WO 91/17130 discloses also a slow release fertilizer composition which includes 70 to 90% of dry weight manure material, 30-10% of dry weight carbohydrate material and water. Carbohydrate material is for example molasses, processed grease trap waste, industrial sugar syrup, starch or brewery waste.

As a conclusion, traditional fertilizers and methods for fertilizing the soil have several drawbacks. Nutrients are added to soil in slight excess in order to meet the requirements of plants. This results in both environmental problems such as eutrophication and also increased biochemical binding of nutrients e. g. into the humus fraction in cultivated land. Bound nutrients are not easily available for use of the plant. Further, traditional fertilization consumes our limited natural sources and energy. Thus there is a need for fertilizer products that at least reduce these problems.

OBJECTS AND SUMMARY OF THE INVENTION

An object of this invention is to provide alternative ways of feeding soil using novel fertilization compositions (fertilizers) comprising at least carbon and nitrogen sources. Particularly the object is to provide fertilizer that enhances function of natural soil bacteria resulting in enhanced microbial activity and thereby availability of mineralized nutrients in soil and activated humus biosynthesis. Further object of the invention is a fertilizer composition for promoting biogas production and composting.

These and other objects are achieved by the present invention as described and claimed below.

The first aspect of the invention is a fertilizer composition (fertilizer). Characteristic features of the fertilizer are given in the characterizing part of claim 1.

The second aspect of the invention is a method for fertilizing soil; both feeding soil bacteria and fertilizing plant. According to the invention the method comprises applying priming carbon and nitrogen in pC:N ratio of 9:1 to 1:1 and optionally other nutrients to the soil.

The third aspect of the invention is a method for manufacturing the fertilizer. According to the invention the method comprises:
(a) providing a carbon source and nitrogen source, and optionally silica and one or more further other nutrient;
(b) forming a mixture of components;
(c) optionally drying said mixture to decrease water content of wet or moist mixture.

The fourth and fifth aspects of the invention are uses of said fertilizer for feeding soil bacteria and fertilizing plant and for promoting biodegradation of thatch in all kinds of lawns.

The sixth aspect of the invention is a fertilizer composition for accelerator for compost or biogas production. According to the invention the composition comprises:
(a) a priming carbon source comprising plant or animal derived fat or mono- or disaccharides or any mixture thereof; and
(b) a source of nitrogen,
wherein the pC/N ratio for the priming carbon of the fertilizer is below 1:1.

The seventh aspect of the invention is the use of the fertilizer composition comprising priming carbon and nitrogen in ratio of pC:N below 1:1 for promoting biodegradation in bio gas production and composting processes.

DETAILED DESCRIPTION OF THE INVENTION

The inventors have surprisingly found that the endogenous soil nutrient resources can be up taken by the plant when degradative action of soil bacteria is first been induced by providing a balanced combination of easily available carbon and nitrogen source. This results that lower amount of added nutrients suffices.

The present invention provides a novel fertilizer product that utilizes the soil nutrient resources, even so, that during the growing season about one half of the nutrients needed by the cultivation plants are available from the soil. The fertilizer utilizes a positive priming effect caused by the addition of easily available priming carbon and nitrogen sources, which induce the natural soil bacteria to fast growth and reproduction. This activation can be optimized by secondary nutritional means, which include one or more of the following: a phosphorus source, a micronutrient source, a source for secondary nutrients, and a silicate fraction. For this activation plant-available nutrients are preferred. Potassium is of course needed for the plants. After fast utilization of the added easily available priming carbon, the now stronger soil bacteria populations attack soil organic carbon resources for carbon. The bacteria excrete extracellular enzymes to degrade the challenged carbon source. The soil bacteria populations start to fall back to the stabilized equilibrium stage, but the enzymes will continue the degrading of the soil organic matter, and release soil-bound plant-available nutrients for cultivation use. The nutrients from the lysis of dead soil bacteria will also be plant-available.

One further advance of the fertilizer of this invention is that industrial and agricultural by-products can be used as a component or a starting material of the fertilizer. Thus the composition saves natural resources and is cost effective compared to traditional fertilization compositions.

In addition to the above-mentioned advantages, the fertilizer has a direct benefit to the environment by reducing the pollution of the groundwater and eutrophication of freshwater ponds, lakes, streams and the Baltic Sea when the cultivation areas where the fertilizer is used are located close to said areas.

It is understood that also nitrogen sources and sources of other nutrients must contain nutrients in form that is available for use by soil bacteria and/or plant.

Phrases such as "carbon source" or "nitrogen source" mean material that contains at least carbon or nitrogen, respectively, but may contain also other constituents than pure carbon or nitrogen in pure or essentially pure form. The carbon and nitrogen can be in any form.

In this connection phrases "easily available carbon", "easily available priming carbon", "priming carbon" and "added carbon" means such carbon, that can be readily up taken by soil bacteria, i.e. soluble carbohydrates, particularly mono- and disaccharides and plant and animal fats (see below). "Primed carbon" means carbon released from soil organic matter by the soil bacteria induced to strong growth and reproduction by easily-available priming carbon. Same applies for the other nutrients respectively. An aspect of the invention is a fertilizer product comprising priming carbon (pC) source, more exactly easily available carbon source, such as mono- and disaccharides and plant and animal fat, readily usable for soil bacteria. Characteristic to said fertilizer is that it comprises a priming carbon source comprising more than 5% by weight, preferably more than 10% by weight, more preferably more than 15% by weight, still more preferably more than 20% by weight, and most preferably at least 30% by weight of plant or animal fat or mono- or disaccharides or any mixture thereof; and a source of nitrogen (N). Typical priming carbon source comprises from 30 to 40% by weight of plant or animal fat or mono- or disaccharides or any mixture thereof. The priming carbon forms preferably at least 33% by weight and more preferably at least 40% by weight of the total carbon of the fertilizer. Plant fat comprises rapeseed, olive, sunflower, palm, yatropha or other corresponding plant oil, and animal fat the classes 2 and 3 of rendered animal fat according to the European legislation of animal byproducts (Commission Regulation (EU) No 142/2011, European Parliament and the Council Regulation (EC) No 1069/2009). Glucose is used most typically as the monosaccharide and sucrose as the disaccharide. Added priming carbon and nitrogen activate soil bacteria which enhance the degradation of soil organic matter and thereby availability of nutrients bound to soil.

In said fertilizer the amount of easily available carbon in said carbon source is 2 to 35%, preferably 5 to 35%, more preferably 10 to 35%, and most preferably 20 to 30% by weight calculated from the dry weight of the fertilizer. The amount of carbon to be added is dependent on the organic carbon content in the soil and on the microbial carbon content in the organic carbon (Table 1). Typical amounts in an average Finnish agricultural soil (3% by weight organic carbon in soil, 0.6% by weight of microbial carbon in organic carbon) amounts from 100 to 350 kg/ha, preferably from 200 to 300 kg/ha of added priming carbon. In warmer climate countries soil microbial activity is usually higher, which means that less soil organic matter is needed for same priming effect level. This results that the upper limit of the linearity range of the primed carbon vs. pC/mC curve will be lower, which also means better possibility to achieve the wanted benefits.

The amount of nitrogen in said nitrogen source is 2 to 8% by weight calculated from the dry weight of the fertilizer. Typically amount of nitrogen is lower than when traditional inorganic fertilizer is used.

The amount of priming carbon is individually adapted to the needs of soil bacteria and the amount of nitrogen to the needs of both soil bacteria and cultivated plant. The proper C/N ratio for the priming carbon (pC/N, calculated from their weights or their weight proportions) in this fertilizer is between 12:1 and 1:1, preferably between 9:1 and 1.5:1 or 8:1 and 1.5:1 or 9:1 and 1:1, more preferably between 7:1 and 3:1, still more preferably between 7:1 and 2.5:1, and most preferably between 7:1 and 2:1.

Table 1 describes the dependencies between the added amount of priming carbon (pC), the microbial carbon (mC) content in the organic carbon, and the primed carbon (PEC) and primed nitrogen (PEN) as an estimate for soils with 3% by weight of organic carbon in cases where 50 kg/ha of added nitrogen will be used. For example, addition of 300 kg/ha of pC into the soil with 1.0% by weight mC will induce 900 kg/ha PEC and 60 kg/ha PEN. In a similar way other primed nutrients will be released.

Preferably the priming carbon source in the fertilizer product is an industrial or agricultural by-product which is accepted or will be accepted for use as a fertilizer or soil amendment. Suitable carbon sources selected from group comprising used industrial silicate clay or other filter beds from filtering fat of biological origin, hydrolysed industrial starch waste fractions, industrial cellulosic wastes such as the fiber sludge, as such or as hydrolysed, various mono- and disaccharide fractions from sugar industries and the mixtures thereof. The fiber sludge of pulp and paper industry, which contain the too short and too long fibers from the pulping and papermaking processes, nowadays lignocelluloses, are a good and inexhaustible source for priming carbon. Lignocelluloses are comprised of about 70% by weight of cellulose and hemicelluloses and about 30% by weight of lignin. Of these cellulose and hemicelluloses are biodegraded and used by soil microorganisms of about few percentages/year and lignin goes to humus biosynthesis thus improving soil structure. The biodegradation of lignocelluloses can be accelerated by the use of the fertilizer of this invention, composted lignocelluloses and the enzymes developed for biodegradation of lignocelluloses for bio ethanol production and their combinations. One way to utilize this carbon source is to spread fiber sludge as soil amendment in the autumn and next spring a proper composition of the fertilizer of this invention is used. Compost from lignocelluloses biodegradation and/or lignocelluloses biodegrading enzymes may be used as raw materials of the fertilizer.

TABLE 1

Various amounts of priming carbon (pC) to be added with 50 kg/ha of fertilizer nitrogen into soils containing 3% by weight organic carbon and various contents of microbial carbon (mC), and primed carbon (PEC) and primed nitrogen (PEN) predicted to be released from the soil organic matter by soil bacteria in nutritionally optimized conditions.

| pC/mC, %* | mC, 0.2% | mC, 0.4% | mC, 0.6% | mC, 0.8% | mC, 1.0% | mC, 1.2% | mC, 1.4% |
|---|---|---|---|---|---|---|---|
| Priming carbon (pC) to be added, kg/ha* | | | | | | | |
| 10 | C:N < 1 | C:N < 1 | C:N < 1 | 60 | 75 | 90 | 105 |
| 20 | C:N < 1 | 60 | 90 | 120 | 150 | 180 | 210 |
| 30 | C:N < 1 | 90 | 135 | 180 | 225 | 270 | 315 |
| 40 | 60 | 120 | 180 | 240 | 300 | 360 | 420 |
| 50 | 75 | 150 | 225 | 300 | 375 | 450 | 525 |
| 60 | 90 | 180 | 270 | 360 | 450 | 540 | C:N > 12 |
| 70 | 105 | 210 | 315 | 420 | 525 | C:N > 12 | C:N > 12 |
| 80 | 120 | 240 | 360 | 480 | 600 | C:N > 12 | C:N > 12 |
| 90 | 135 | 270 | 405 | 540 | C:N > 12 | C:N > 12 | C:N > 12 |
| 100 | 150 | 300 | 450 | 600 | C:N > 12 | C:N > 12 | C:N > 12 |
| Release of primed carbon (PEC) by soil bacteria from soil organic matter, kg/ha** | | | | | | | |
| 10 | n.e. | n.e. | n.e. | 180 | 225 | 270 | 315 |
| 20 | n.e. | 180 | 270 | 360 | 450 | 540 | 630 |
| 30 | n.e. | 270 | 405 | 540 | 675 | 810 | 945 |
| 40 | 180 | 360 | 540 | 720 | 900 | 1080 | 1260 |
| 50 | 225 | 450 | 675 | 900 | 1125 | 1350 | 1575 |
| 60 | 270 | 540 | 810 | 1080 | 1350 | 1620 | n.e. |
| 70 | 315 | 630 | 945 | 1260 | 1575 | n.e. | n.e. |
| 80 | 360 | 720 | 1080 | 1440 | 1800 | n.e. | n.e. |
| 90 | 405 | 810 | 1215 | 1620 | n.e. | n.e. | n.e. |
| 100 | 450 | 900 | 1350 | 1800 | n.e. | n.e. | n.e. |
| Release of primed nitrogen (PEN) by soil bacteria from soil organic matter, kg/ha*** | | | | | | | |
| 10 | n.e. | n.e. | n.e. | 12 | 15 | 18 | 21 |
| 20 | n.e. | 12 | 18 | 24 | 30 | 36 | 42 |
| 30 | n.e. | 18 | 27 | 36 | 45 | 54 | 63 |
| 40 | 12 | 24 | 36 | 48 | 60 | 72 | 84 |
| 50 | 15 | 30 | 45 | 60 | 75 | 90 | 105 |
| 60 | 18 | 36 | 54 | 72 | 90 | 108 | n.e. |
| 70 | 21 | 42 | 63 | 84 | 105 | n.e. | n.e. |
| 80 | 24 | 48 | 72 | 96 | 120 | n.e. | n.e. |
| 90 | 27 | 54 | 81 | 108 | n.e. | n.e. | n.e. |
| 100 | 30 | 60 | 90 | 120 | n.e. | n.e. | n.e. |

| pC/mC, %* | mC, 1.6% | mC, 1.8% | mC, 2.0% | mC, 2.2% | mC, 2.4% | mC, 2.6% | mC, 2.8% | mC, 3.0% |
|---|---|---|---|---|---|---|---|---|
| Priming carbon (pC) to be added, kg/ha* | | | | | | | | |
| 10 | 120 | 135 | 150 | 165 | 180 | 195 | 210 | 225 |
| 20 | 240 | 270 | 300 | 330 | 360 | 390 | 420 | 450 |
| 30 | 360 | 405 | 450 | 495 | 540 | 585 | C:N > 12 | C:N > 12 |
| 40 | 480 | 540 | 600 | C:N > 12 | C:N > 12 | C:N > 12 | C:N > 12 | C:N > 12 |
| 50 | 600 | C:N > 12 | C:N > 12 | C:N > 12 | C:N > 12 | C:N > 12 | C:N > 12 | C:N > 12 |
| 60 | C:N > 12 | C:N > 12 | C:N > 12 | C:N > 12 | C:N > 12 | C:N > 12 | C:N > 12 | C:N > 12 |
| 70 | C:N > 12 | C:N > 12 | C:N > 12 | C:N > 12 | C:N > 12 | C:N > 12 | C:N > 12 | C:N > 12 |
| 80 | C:N > 12 | C:N > 12 | C:N > 12 | C:N > 12 | C:N > 12 | C:N > 12 | C:N > 12 | C:N > 12 |
| 90 | C:N > 12 | C:N > 12 | C:N > 12 | C:N > 12 | C:N > 12 | C:N > 12 | C:N > 12 | C:N > 12 |
| 100 | C:N > 12 | C:N > 12 | C:N > 12 | C:N > 12 | C:N > 12 | C:N > 12 | C:N > 12 | C:N > 12 |
| Release of primed carbon (PEC) by soil bacteria from soil organic matter, kg/ha** | | | | | | | | |
| 10 | 360 | 405 | 450 | 495 | 540 | 585 | 630 | 675 |
| 20 | 720 | 810 | 900 | 990 | 1080 | 1170 | 1260 | 1350 |
| 30 | 1080 | 1215 | 1350 | 1485 | 1620 | 1755 | n.e. | n.e. |
| 40 | 1440 | 1620 | 1800 | n.e. | n.e. | n.e. | n.e. | n.e. |
| 50 | 1800 | n.e. | n.e. | n.e. | n.e. | n.e. | n.e. | n.e. |
| 60 | n.e. | n.e. | n.e. | n.e. | n.e. | n.e. | n.e. | n.e. |
| 70 | n.e. | n.e. | n.e. | n.e. | n.e. | n.e. | n.e. | n.e. |
| 80 | n.e. | n.e. | n.e. | n.e. | n.e. | n.e. | n.e. | n.e. |
| 90 | n.e. | n.e. | n.e. | n.e. | n.e. | n.e. | n.e. | n.e. |
| 100 | n.e. | n.e. | n.e. | n.e. | n.e. | n.e. | n.e. | n.e. |

TABLE 1-continued

Various amounts of priming carbon (pC) to be added with 50 kg/ha of fertilizer nitrogen into soils containing 3% by weight organic carbon and various contents of microbial carbon (mC), and primed carbon (PEC) and primed nitrogen (PEN) predicted to be released from the soil organic matter by soil bacteria in nutritionally optimized conditions.

Release of primed nitrogen (PEN) by soil bacteria from soil organic matter, kg/ha***

| | | | | | | | | |
|---|---|---|---|---|---|---|---|---|
| 10 | 24 | 27 | 30 | 33 | 36 | 39 | 42 | 45 |
| 20 | 48 | 54 | 60 | 66 | 72 | 78 | 84 | 90 |
| 30 | 72 | 81 | 90 | 99 | 108 | 117 | n.e. | n.e. |
| 40 | 96 | 108 | 120 | n.e. | n.e. | n.e. | n.e. | n.e. |
| 50 | 120 | n.e. | n.e. | n.e. | n.e. | n.e. | n.e. | n.e. |
| 60 | n.e. | n.e. | n.e. | n.e. | n.e. | n.e. | n.e. | n.e. |
| 70 | n.e. | n.e. | n.e. | n.e. | n.e. | n.e. | n.e. | n.e. |
| 80 | n.e. | n.e. | n.e. | n.e. | n.e. | n.e. | n.e. | n.e. |
| 90 | n.e. | n.e. | n.e. | n.e. | n.e. | n.e. | n.e. | n.e. |
| 100 | n.e. | n.e. | n.e. | n.e. | n.e. | n.e. | n.e. | n.e. |

*Priming carbon:microbial carbon ratio (pC/mC, % by weight). In practice the added amount of priming carbon is restricted by the nitrogen content of the fertilizer: C:N ≤ 12:1, otherwise the start of plant growth may suffer for the lack of nitrogen; C:N ≥ 1:1, otherwise the priming effect benefits are negligible (<10 kg PEN/ha).
**Primed carbon released from soil organic matter by soil bacteria. Estimation is based on optimized nutritional conditions for soil bacteria to grow and reproduce. n.e., not estimated (C:N > 12, C:N < 1:1).
***Primed nitrogen (PEN) released from soil organic matter by soil bacteria. n.e., not estimated (C:N > 12:1 or < 1:1)

Preferably the nitrogen source is an organic nitrogen source or ammonium nitrogen source or a combination of both. Suitable organic nitrogen sources include industrial and agricultural nitrogenous side products (by-products) and their mixtures, such as meat and bone meal, blood meal, meat meal, fish meal, feather meal, soybean meal, cottonseed meal, rapeseed scrub, linseed scrub, organic nitrogen containing fertilizers and soil amendments, separation mixture from betaine production, vinasse or other fermentation remains e.g. from bioethanol production, manure fractions in all technical forms such as pig slurry, cattle manure sludge, poultry manure, horse manure, compost, rotting residues and reject water. Ammonium nitrogen sources include urea and various ammonium salts and urea and ammonium containing fertilizers.

It is essential for this fertilizer to work that the nitrogen fertilization level is lower than usually. It should be from 10 to 90% by weight, preferably from 20 to 80% by weight, more preferably from 30 to 70% by weight, still more preferably from 40 to 70% by weight, and most preferably from 50 to 70% by weight of the common fertilization level calculated per hectare.

The organic nitrogen sources mentioned above contain besides the nitrogen also comprehensive amounts of biodegradable carbon. This carbon is easy food for the by the fertilizer of this invention strengthened and enriched soil microbial populations due to their optimal pC:N ratio and fresh nitrogen and carbon sources. Soil organic matter instead has been the object of biodegradation already for several years (in practice from one to over hundred years). So, these organic nitrogen sources will be biodegraded first, and after them the soil organic matter. It is thus important, that the total carbon content of the fertilizer is not too high in relation to the priming carbon content because the strengthened soil bacteria populations will use this extra organic carbon as their carbon source instead of the soil organic carbon. A proper rule of thumb is that one part of extra organic carbon will diminish the positive priming effect by one third. Thus the priming carbon content should be at least 33% by weight, preferably at least 40% by weight, more preferably at least 45% by weight, still more preferably at least 50% by weight, and most preferably at least 55% by weight. It is also important to keep the amount of the added carbon in the optimum range e.g. as presented in Table 1 otherwise nitrogen immobilization and negative priming effect may result which leads the plants to suffer for lack of nitrogen.

Preferably both carbon and nitrogen are organic and thus the resulting fertilizer is suitable for organic cultivation.

In one embodiment of the invention the fertilizer further comprises one or more of the following
(a) phosphorus source
(b) secondary nutrient source,
(c) micronutrient source
(d) potassium source; and optionally
(e) a silicate source, wherein silicate fraction is 10 to 60% by weight calculated from dry weight of the fertilizer.

In still further embodiment the fertilizer further comprises additives accepted for use in fertilizers.

Additives are used as binders, fillers, processing aids or coating agents and selected from plant and animal fat, lignins and industrial sugar production by-products, without restricting to those.

In this connection the term "micronutrient" means a source of nutrient selected from the group: copper (Cu), iron (Fe), manganese (Mn), molybdenum (Mo), zinc (Zn) and cobalt (Co). Iron and manganese have strong redox potential and thus they activate microbial cell respiration, degradation of soil organic matter and humus biosynthesis. Zinc, copper, cobalt and molybdenum are microbial enzyme activators. Micronutrients are applied as salts, and bound to organic or mineral raw materials.

In this connection the term "secondary nutrient" is preferably calcium (Ca), magnesium (Mg) and sulphur (S), which can be added e.g. by chalking the soil to optimized pH with calcium silicate or blast or steel furnace slag. Secondary nutrient sources are usually low in nutrient content and huge amounts are generally needed. Secondary nutrients are thus spread separately as needed and are not included as structural part of the fertilizer.

It is understood to a man skilled in the art that amount of nutrients is greatly dependent of e.g. the properties of the soil and cultivated plant. Skilled man is able to estimate the particular needs in each situation. However, when the fertilizer of this invention is used, the amount of nutrients needed is typically lower compared to situation where traditional fertilizer is used. And this is because of the optimization of the nutritive circumstances by the fertilizer for the soil bacteria to grow and reproduce, and thus degrade soil organic matter optimally to release nutrients for the plants.

Preferably the amount of soluble phosphorus in the fertilizer product of the invention is less than 0.5% by weight, calculated from dry weight of the fertilizer.

Preferably the amount of silicate in the fertilizer product of the invention is at least 10% by weight calculated from dry weight of the fertilizer. Silicate is used as a filler material in the fertilizer. It increases the porosity and ion-exchange capacity in the soil and has surface catalytic effects for organic matter biodegradation and humus biosynthesis.

Preferably the phosphorus source is a selected from an organic phosphorus source, a mineral phosphorus source and a combination thereof. Suitable phosphorus sources include meat and bone meal, bone meal, feather meal, used industrial silicate clay or other filter beds from filtering fat of biological origin, manure based agricultural side products, manure fractions in any technical form such as pig slurry, cattle manure sludge, poultry manure, horse manure and some recycled raw materials, such as sewage sludge, as such or composted or rotted, various composts and rotting residues from biogas production. Mineral phosphorus sources include various phosphorus salts, apatite and phosphorus containing fertilizers. Organic farming accepts all other phosphorus sources except the salt forms.

In one embodiment the amount of phosphorus in said phosphorus source is 0.5 to 3% by weight calculated from dry weight of the fertilizer.

Preferably the silicate fraction comprises used industrial silicate clay filtering beds from filtering fat of biological origin, calcium silicate and/or silicate mineral or a mixture thereof. The used silicate clay filter beds from fat filtering are preferred.

Preferred embodiments of fertilization compositions optimized to various needs are given in the Table 2 below.

Table 2 shows preferred embodiments of fertilizer compositions of the invention and suitable uses.

| Fertilizer | pC, % | tC, % | N, % | pC/N | tC/N | Use |
|---|---|---|---|---|---|---|
| NPK 8-3-1 | 23.0 | 23.0 | 8.2 | 2.8 | 2.8 | Thatch eater |
| NPK 4-2-4 | 17.5 | 29.6 | 4.0 | 4.3 | 7.4 | Thatch eater |
| NPK 4-2-2 | 18.2 | 33.3 | 4.4 | 4.1 | 7.6 | Cereals |
| NPK 4-0.5-2 | 13.8 | 17.8 | 4.3 | 3.2 | 4.1 | Cereals |
| NPK 5-3-1 | 18.1 | 33.8 | 4.6 | 3.9 | 7.4 | Cereals |
| NPK 4-2-2 | 19.6 | 33.4 | 3.9 | 5.1 | 8.6 | Cereals | pC, priming carbon; tC, total carbon; N, nitrogen

One aspect of the invention is a method for fertilizing soil comprising applying priming carbon, nitrogen and optionally other nutrients to the soil. Suitable fertilizing compositions have been discussed above.

Within this invention it is possible to apply various nutrients in separate steps. Especially for high nutrient needs or for sources of low nutrient content it is more convenient to fertilize some components separately. When carbon need is high, it may be advisable to apply, e.g. 2 t/ha of carbon source separately, and then the rest in conventional time or when needed. Sometimes the nutrients may be applied together with e.g. sludge manures, which are poor in nutrients.

In one embodiment of the invention the carbon source is applied as a separate step. The other nutrients are mixed with e.g. sludge manure and applied in conventional time or when needed.

In one embodiment of the invention the low content nitrogen and phosphorus source is applied separately, and the rest of the components are applied in conventional time or when needed.

The fertilizer composition is suitable to be applied in any known method such as granulates, powder or a liquid composition. Composition can be used as such or admixed with manure, manure sludge or other components to be applied to the cultivated soil.

One aspect of the invention is a method for manufacturing the fertilizer. The method comprises steps of:
(a) providing a priming carbon source and nitrogen source, and optionally silica and one or more further other nutrient and/or additive; and
(b) forming a dry or wet mixture of components; and
(c) optionally drying said mixture to decrease water content of wet or moist mixture.

Components used in the method can be essentially dry, they can be moist or slurry that contains dissolved partially dissolved and/or solid materials. Liquid fertilizer (fertilizer slurry) is dried to form solid fertilizer or it is concentrated or used as such. Suitable dry matter content depends on the application. Dry fertilizer product contains at least 85% by weight dry matter. Powdered compositions are dry. Mixtures with humidity from 8 to 22% by weight are suitable for granulation.

Granulated or powdered product is obtained by forming the mixture having suitable humidity into granulated or powdered fertilizer.

Granules are formed using conventional methods. They can be coated. It is also possible to crush and screen the granules in order to obtain smaller granules/crude powder that is easy to apply.

Preferably said priming carbon source and/or nitrogen source is industrial or agricultural by-product and provided in amount calculated based on actual carbon or nitrogen content of said source.

Preferably, the silicate fraction and easily available carbon source is added as used silicate filter bed from filtering fat of biological origin.

One embodiment of the invention is a use of the fertilizer as described here for fertilizing soil bacteria and plant. Preferably the fertilizer is used for agricultural plant production, gardens, sport fields, parks, public green areas and forest. Advantages of the fertilizer of this invention are described above.

In one embodiment the fertilizer composition of this invention is applied to golf and other sports field lawns and to park and yard lawns. The fertilizer provides several advantages over traditional maintenance of lawns. The fertilizer simultaneously meets the nutritional needs for prolonged time and also enhances thatch degradation so that no additional "thatch eater treatment" is needed.

In one embodiment the fertilizer of this invention is used on the second year after the first year's organic fertilization. In this way the plant-availability of the unused nutrients of the first year's organic fertilization will be remarkably enhanced on the second year.

One embodiment of the fertilizer of this invention is its use on the second year after the first year's soil improvement with forest industrial fiber sludge. The fertilizer will increase the biodegradability of lignocelluloses and enhance the bioavailability of its cellulose and hemicelluloses constituents as the priming carbon source of the soil bacteria, and is by this way enhancing soil fertility and mineralization of soil organic matter to release nutrients for the cultivation plants.

This invention is directed also to a fertilizer composition for accelerator for compost or biogas production comprising:
(a) a priming carbon source comprising plant or animal derived fat or mono- or disaccharides or any mixture thereof; and
(b) a source of nitrogen, wherein the pC/N ratio for the priming carbon of the fertilizer is below 1:1.

Preferably the pC/N ratio of the composition for use as accelerator in biogas production or for compost is from 0.1:1 to 0.8:1, more preferably from 0.1:1 to 0.5:1. Optimal pC/VS ratio is from 0.005:1 to 0.05:1, preferably from 0.005:1 to 0.04:1, 0.04:1 to 0.05:1, more preferably from 0.005:1 to 0.03:1, 0.03:1 to 0.05:1 and most preferably from 0.005:1 to 0.02:1, 0.02:1 to 0.05:1.

In one embodiment the fertilizer of this invention is used to accelerate the rotting process to enhance biogas yield in biogas production processes.

In one embodiment the fertilizer of this invention is used as compost accelerator to fasten the composting process.

Within the above uses of the fertilizer of this invention as accelerator for the rotting and composting processes, when plants are missing and only compost microbes are nourished, the last two requirements of claim 1 concerning the C/N ratio limits for priming carbon and the proportion limit for the priming carbon of the total carbon are not valid. In rotting and composting processes the amounts of total nitrogen and total carbon are usually high in relation to the added priming carbon resulting in low C/N ratios and low proportions for the priming carbon of the total carbon. When the fertilizer of this invention is utilized as rotting or composting accelerator, the C/N ratio for the priming carbon of the fertilizer needs to be below 15 and is usually below 2 for pC/N $H_4$—N and below 1 for pC/N. The priming carbon of the fertilizer should comprise 0.5 to 5% by weight, more preferably 4 to 5, 0.5 to 4% by weight, still more preferably 3 to 5, 0.5 to 3% by weight and most preferably 2 to 5, 0.5 to 2% by weight of the volatile substances (VS) of the biodegradable matter to be rotted or composted.

The invention is illustrated by the following non-limiting examples. It should be understood that the embodiments given in the description above and the examples are for illustrative purposes only, and that various changes and modifications are possible within the scope of the invention.

EXAMPLES

Example 1

Field Experiment, Priming with Glucose

In one field experiment on a farm yard in the summertime two groups of thuja plants were tested within similar watering, fertilization and other conditions. The thujas were growing in 50 liter pots in ordinary humus soil for flowers. Small portions of 10% by weight glucose solution (5 g carbon/day) were applied as a carbon source for 100 days for one thuja plant with a total of 500 g C/50 kg soil, or 1% by weight or 25 tons C/ha for the growing season. In autumn this thuja plant was much more vital than the thuja plants in the control group.

Without binding to the theory, the daily glucose addition has been the priming carbon source for soil bacteria: the added glucose and the fertilizer nitrogen together have nourished the soil bacteria populations to strong growth and reproduction until the daily glucose dose has been used. Thereafter the soil bacteria have started to use soil organic matter as their carbon source and release nitrogen from the soil organic matter to be used by the thuja plant.

Example 2

Field Experiments with Fertilizer

In another field experiment 15 kg (75% by weight) of used industrial silicate clay filter bed from fat filtering, 3 kg (15% by weight) of urea, 1 kg (5% by weight) of ferrous sulfate heptahydrate (1% by weight of iron) and 1 kg (5% by weight) of diammonium phosphate (DAP) were mixed. One kg of the resulted fertilizer mixture (NPK 8-3-1, 40 kg N/ha, 110 kg pC/ha) was applied in late summer for 20 $m^2$ of yard lawn. After one month, in comparison with unfertilized control plot, the fertilized plot looked out much more vital. Comparison of a NPK 8-3-1 with pC fertilized plot with a NK 8-8 fertilized (without carbon) plot (1 kg for 20 $m^2$, 40 kg N/ha) did not show any differences by sight.

It is assumed, that the added fertilizer-fat-carbon and fertilizer-nitrogen together have nourished the soil bacteria populations to grow and reproduce. After the fat-carbon has been consumed the soil bacteria have started to break down the soil organic matter for their carbon needs and release nutrients to be used by the grass.

This preliminary experiment had bad timing (1 month in autumn). Nevertheless the lacks, the fertilizer with carbon (NPK 8-3-1, 23% by weight pC) gave the same result with much lower raw material costs (53% vs. 100%) as compared with the NK 8-8 (no carbon) fertilization.

Example 3

Thatch Eater Application

In a thatch eater application, the above NPK 8-3-1 fertilizer (500 kg/ha, 40 kg N/ha, 110 kg pC/ha) was applied for an old thatched golf green in late summer together with a NK 8-8 (no carbon, 500 kg/ha, 40 kg N/ha) application. Both applications were on the holed green, after which the holes were filled with sand. Both experiments were compared with an unfertilized part of the green, with an older application with a commercial enzymes based thatch eater on a nearby green, and with each other. After one month, clear vitalizing and softening of both fertilized greens were found. Principal action was better for both fertilized greens compared with control and the commercial thatch eater.

The basis for the NPK 8-3-1 thatch eater lies on the fat-carbon (priming carbon) nourishment of soil bacteria which, after the primary strong growth and reproduction step, start to use thatch as their priming carbon source. The NK 8-8 thatch eater nourishes the soil bacteria with organic carbon, mineral and organic nitrogen and low-phosphorus, thus promoting thatch-eating.

This result demonstrates that the fertilizer of the invention serves also as a thatch degradation promoting agent. Based on earlier experiments it is also believed that the fertilizing effect of carbon containing fertilizer will extend the time between the fertilizations.

Example 4

Field Experiment with Barley

In a field experiment with barley two fertilizer compositions were tested and compared with a commercial organic fertilizer Viljo NPK 8-5-1 (Novarbo, Finland). The first test fertilizer (Fertilizer I) was constructed of 50% by weight meat and bone meal, 40.5% by weight used industrial silicate clay filter bed from fat filtering, 9% by weight concentrated separation mixture from betaine production and 0.5% by weight ferrous sulfate heptahydrate. It was used 1247 kg/ha and comprised as main nutrients 54.3 kg/ha nitrogen, 54.6 kg/ha phosphorus and 15 kg/ha potassium. C:N ratio for the priming carbon of the fertilizer I was 3.9:1.

The second test fertilizer (Fertilizer II) was constructed of 41% by weight meat and bone meal, 48% by weight used industrial silicate clay filter bed from fat filtering, 11% by weight concentrated separation mixture from betaine production and 1% by weight ferrous sulfate heptahydrate. It was used 1487 kg/ha and comprised as main nutrients 54.7 kg/ha nitrogen, 49.1 kg/ha phosphorus and 21.1 kg/ha potassium. C:N ratio for the priming carbon of the fertilizer II was 5.1:1. Viljo fertilizer NPK 8-5-1 was added 1243 kg/ha corresponding 92.1 kg/ha nitrogen, 58.9 kg/ha phosphorus and 11.4 kg/ha potassium. The soil consisted of mineral matter from fine sand to sand containing 3.35% by weight organic carbon and 0.26% by weight total nitrogen thus having a C:N ratio of 12.9:1. Soil fertility was mainly in good condition, but manganese showed a bit low level and calcium and magnesium a bit high level.

The fertilizers were spread on 22 May 2012 on 2.5 m*350 m test squares each, after which barley Tiple was sawed on the next day. The crops were harvested on $10^{th}$ September and sampled on the same day from area of 1 m*10 m square each. The crop samples were air dried to selling moisture where after the grains were analyzed.

The crop analysis data for the test fertilizers is presented as kg/kg N/ha in Table 3. Fertilizers I and II showed very similar results when compared with each other but much better results (up to 80%) when compared to the commercial organic Viljo NPK 8-5-1 fertilizer. Without binding to the theory, the fertilizers I and II feed the native soil bacteria for a rapid and strong growth and reproduction, which after consuming the easily available carbon of the fertilizer leads in fastened soil organic matter degradation and release of its plant nutrients for crop production.

The nitrogen balance of the fertilizers I and II calculated as the difference between the input (fertilizer-N, kg/ha) and output (feed protein-N, kg/ha) showed high nitrogen efficiency for both fertilizers: fertilizer I, 54.3 kg N/ha (input)–52.1 kg N/ha (output)=2.2 kg N/ha (4% by weight); fertilizer II, 54.7 kg N/ha–55.1 kg N/ha=–0.4 kg N/ha (–0.7% by weight)(Table 3). 4% by weight of the nitrogen of the fertilizer I was left in the soil, but the fertilizer II took 0.7% by weight of the crop-nitrogen from the soil. These results are in agreement with their pC-contents and pC:N ratios (fertilizer II had higher pC content and higher pC:N ratio, which indicates higher primed carbon from the soil; for comparison Viljo NPK 8-5-1, 92.1 kg N/ha–53.1 kg N/ha=39.0 kg N/ha (42% by weight), which means that 42% by weight of the fertilizer-nitrogen was left in the soil).

TABLE 3

Total crop, starch crop and feed protein crop obtained with the test fertilizers in the field experiment with Tiple barley. The crop obtained using Fertilizers I or II has been given also as percentages of a control crop, i.e. crop obtained using Viljo NPK 8-5-1 fertilization (percentage value 100; percentages calculated by weight)

|  | Total crop | | Starch crop | | Feed protein crop | |
| --- | --- | --- | --- | --- | --- | --- |
|  | kg/kg N/ha | % | kg/kg N/ha | % | kg/kg N/ha | % |
| Fertilizer I | 71 | 177 | 31 | 180 | 6.0 | 167 |
| Fertilizer II | 72 | 180 | 31 | 179 | 6.3 | 175 |
| Viljo NPK 8-5-1 | 40 | 100 | 17 | 100 | 3.6 | 100 |

Example 5

Pot Experiment with Annual Rye Grass Demonstrating the Dependence of Priming Fertilization on Soil Microbial Carbon Content In this annual ryegrass pot experiment an organic NPK 4-2-2 test fertilizer (Fertilizer III, 18.2% by weight priming carbon (pC), pC:N 4.1:1) and a mineral NPK 4-0.5-2 test fertilizer (Fertilizer IV, 13.8% by weight priming carbon, pC:N 3.2:1) were compared with an organic commercial meat and bone meal based fertilizer Perus-Viljo NPK 8-3-1 (Elosato, Finland) (4.1% by weight priming carbon, pC:N 0,56:1) and a mixed mineral fertilizer NPK 17-2-9 (no priming carbon). The organic test fertilizer III was comprised of meat and bone meal (42% by weight), used industrial silicate clay filter bed from fat filtering (42% by weight), ferrous sulfate heptahydrate (0.5% by weight) and concentrated separation mixture from betaine production (16% by weight). The mineral test fertilizer IV was comprised of used industrial silicate clay filter bed from fat filtering (42% by weight), blasting sand (33% by weight), urea (7% by weight), diammonium phosphate (2% by weight), ferrous sulfate heptahydrate (0.5% by weight) and concentrated separation mixture from betaine production (16% by weight). The mineral fertilizer NPK 17-2-9 was mixed from Oulu saltpeter (63% by weight; Kemira GrowHow, Finland), superphosphate (20% by weight; Kemira GrowHow, Finland) and potassium chloride (17% by weight; Kemira GrowHow, Finland).

All four fertilizers were applied as six repeats at five fertilization levels (0, 20, 40, 80 and 160 kg N/ha) by mixing the calculated amounts of each fertilizer with three liters of fine sandy soil (70% by weight)-sand (30% by weight) soil mixture containing 0.7% by weight organic carbon. The fertilized soils in three liter pots were transferred into plant house, and the growing experiment was started with annual rye grass sowing in the week 5/2012. Potassium sulfate was added to complete the potassium nutrition needs of annual rye grass in each pot. The pot experiment comprised a total of 120 pots (4 fertilizers*5 levels*6 repeats). The growing period comprised four cuts (cuttings), after 21 days growth each, so it lasted a total of 84 days. Table 4 shows the annual rye grass crop formation during the pot experiment in low carbon soil.

TABLE 4

Comparison of the fertilizing effects of four fertilizers as annual rye grass crops in low carbon soil. The total crops have been given also as percentages of NPK 17-2-9 and Perus-Viljo NPK 8-5-1 fertilized crops (percentage values 100)

|  | N kg/ha | pC* kg/ha | pC/mC* % | Cut 1** | Cut 2** | Cut 3** | Cut 4** | Total** | % | % |
| --- | --- | --- | --- | --- | --- | --- | --- | --- | --- | --- |
| Fertilizer III | 20 | 86 | 82 | 0.495 | 0.193 | 0.134 | 0.087 | 0.908 | 72.5 | 143.3 |
| Fertilizer IV | 20 | 67 | 64 | 0.047 | 0.073 | –0.038 | –0.003 | 0.080 | 6.4 | 12.6 |

TABLE 4-continued

Comparison of the fertilizing effects of four fertilizers as annual rye grass crops in low carbon soil. The total crops have been given also as percentages of NPK 17-2-9 and Perus-Viljo NPK 8-5-1 fertilized crops (percentage values 100)

| | N kg/ha | pC* kg/ha | pC/mC* % | Cut 1** | Cut 2** | Cut 3** | Cut 4** | Total** | % | % |
|---|---|---|---|---|---|---|---|---|---|---|
| Perus-Viljo | 20 | 21 | 20 | 0.332 | 0.203 | 0.053 | 0.045 | 0.634 | 50.6 | 100.0 |
| NPK 17-2-9 | 20 | 0 | 0 | 0.757 | 0.425 | −0.035 | 0.105 | 1.252 | 100.0 | 197.6 |
| Fertilizer III | 40 | 172 | 164 | 0.719 | 0.478 | 0.224 | 0.109 | 1.530 | 73.4 | 68.3 |
| Fertilizer IV | 40 | 134 | 127 | 0.671 | 0.486 | 0.045 | 0.036 | 1.237 | 59.4 | 55.3 |
| Perus-Viljo | 40 | 41 | 40 | 1.115 | 0.917 | 0.068 | 0.140 | 2.239 | 107.5 | 100.0 |
| NPK 17-2-9 | 40 | 0 | 0 | 1.163 | 0.723 | 0.075 | 0.122 | 2.083 | 100.0 | 93.1 |
| Fertilizer III | 80 | 345 | 328 | 0.917 | 0.765 | 0.439 | 0.204 | 2.325 | 78.7 | 64.2 |
| Fertilizer IV | 80 | 267 | 254 | 1.202 | 0.897 | 0.263 | 0.071 | 2.432 | 82.3 | 67.2 |
| Perus-Viljo | 80 | 83 | 79 | 1.847 | 1.386 | 0.213 | 0.176 | 3.621 | 122.6 | 100.0 |
| NPK 17-2-9 | 80 | 0 | 0 | 1.112 | 1.505 | 0.233 | 0.103 | 2.953 | 100.0 | 81.6 |
| Fertilizer III | 160 | 689 | 656 | 1.730 | 1.512 | 0.715 | 0.319 | 4.276 | 60.6 | 76.0 |
| Fertilizer IV | 160 | 534 | 509 | 1.646 | 2.123 | 0.555 | 0.234 | 4.558 | 64.6 | 81.1 |
| Perus-Viljo | 160 | 166 | 158 | 1.200 | 2.855 | 1.174 | 0.393 | 5.623 | 79.7 | 100.0 |
| NPK 17-2-9 | 160 | 0 | 0 | 2.080 | 3.635 | 1.105 | 0.233 | 7.053 | 100.0 | 125.4 |

*pC, priming carbon; mC, microbial carbon; 0.7% C, 0.0042% mC;
**dry grass, g/pot In this experiment the soil organic carbon content was low, only 0.7% by weight, resulting also in a low soil microbial carbon content, 0.0042% by weight. At the fertilization levels 20, 40, 80 and 160 kg N/ha the test fertilizer III fertilized the soil with 0.82, 1.64, 3.28 and 6.56 g priming carbon/1 g microbial carbon of the soil, respectively (Table 4). Correspondingly, the test fertilizer IV and Perus-Viljo NPK 8-5-1 fertilized the soil with 0.64, 1.27, 2.54 and 5.09 g and 0.20, 0.40, 0.79 and 1.58 g priming carbon per 1 g soil microbial carbon, respectively.

In comparison with the supposed linear range for the primed carbon (PEC) vs priming carbon (pC)/microbial carbon (mC) from 0 up to 100% (Table 1), it is obvious that only the lowest value of the test fertilizers III and IV at the fertilization level 20 kg N/ha are valid. Instead Perus-Viljo is valid in the fertilization levels 20, 40 and 80 kg N/ha. This results, that at the lowest fertilization level (20 kg N/ha) the fertilizer III is expected to induce the highest positive priming effect and yield the highest crop of the priming fertilizers. Table 4 shows, that this is true: the crop obtained with the fertilizer III is over 40% by weight higher as compared to that obtained with Perus-Viljo.

The priming fertilizers bind fertilizer-nitrogen for microbial growth and reproduction. This results in lower amount of plant-available nitrogen at the start of the growing period and delayed growth for the priming fertilizers in comparison with the NPK 17-2-9 fertilizer. Later the release of primed nitrogen will compensate this growth delay. On the lowest fertilization level 20 kg N/ha the real nitrogen fertilization was like follows: fertilizer III, 20−5.7 (nitrogen bound to microbial cells, priming carbon/15 (microbial C:N 5:1))=14.3 kg N/ha (71% by weight); fertilizer IV, 20−4.5=15.5 kg N/ha (78% by weight); Perus-Viljo, 20−1.4=18.6 kg N/ha (93% by weight).

On such a low nitrogen fertilization level the differences between the fertilizers will be pronounced. In the case of the fertilizers III and IV the microbial nitrogen is high because the used priming carbon is overdosed to the soil microbial carbon content by a factor 5-7 (in this case the optimum level for the priming carbon content at the fertilization level 160 kg N/ha would be 105 kg pC/ha; on contrary, optimum level of soil organic carbon content for the used levels of pC of the fertilizers III and IV would be 4-5). On the fertilization level 20 kg N/ha the NPK 17-2-9 fertilizer gave the highest crop. The extremely low crop with the mineral test fertilizer IV at the fertilization level 20 kg N/ha is probably due to the immediate availability of urea-nitrogen for the soil bacteria and its simultaneous delayed availability for plants (the organic test fertilizer III releases its nitrogen slower compared to the mineral test fertilizer IV resulting in strongest positive priming effect compared to the other priming fertilizers on the lowest nitrogen fertilization level 20 kg N/ha).

At the fertilization level 40 kg N/ha Perus-Viljo NPK 8-5-1 showed the best crop, even 7.5% by weight higher over that of the NPK 17-2-9. This is due to the facts that its pC/mC is on the optimum range (<100%) and the fertilization level is high enough (fertilizer III, pC/mC=164% (>100%), 40−11.5=28.5 kg N/ha; fertilizer IV, pC/mC=127% (>100%), 40−8.9=31.1 kg N/ha; Perus-Viljo, pC/mC=40% (<100%), 40−2.8=37.2 kg N/ha; NPK 17-2-9, pC=0, 40−0=40 kg N/ha). Test fertilizer III is now out of the linear (PEC vs pC/mC) range but its relative crop compared with that of the NPK 17-2-9 is still going up. Test fertilizer IV is also out of the proposed linear PEC vs pC/mC range, but less than the fertilizer III. Its crop shows now comprehensive relative increase compared with that of the NPK 17-2-9.

At the fertilization level 80 kg N/ha Perus-Viljo NPK 8-5-1 showed again the best crop, now 22.6% by weight higher than that of the NPK 17-2-9 (pC/mC=79% (<100%), 80−5.6=74.4 kg N/ha). The test fertilizers III and IV have both increased their relative crop compared with the NPK 17-2-9, the crop yield of the latter being now slightly higher.

At the fertilization level 160 kg N/ha the crops of the fertilizers III, IV and Perus-Viljo NPK 8-5-1 were clearly diminished compared with that of NPK 17-2-9 showing comprehensive negative priming effect. pC/mC of all test fertilizers is now out of the proposed linear range (>100%).

This experiment has demonstrated quite clearly the following:
(i) Positive priming effect is dependent on the soil microbial carbon content and hence the soil carbon content.
(ii) Overdosing of priming carbon leads out of the linear pC/mC range, which weakens the positive priming effect and may at last result even in negative priming effect.
(iii) Positive priming effect with the fertilizer III on the fertilization level 20 kg N/ha yielded 43.3% by weight higher annual rye grass crop compared with that of the Perus-Viljo NPK 8-5-1, despite of the low soil organic carbon content, 0.7% by weight (fertilizer III and Perus-Viljo are both on the linear PEC vs pC/mC range, cf. Table 4). In higher soil organic carbon (SOC) contents (optimum level 4-5% by weight SOC for the used pC levels of the fertilizers III and IV) the positive priming effect is predicted to be on the same level (40-45% by weight) at least on the fertilization level 80 kg N/ha.
(iv) Positive priming effect with the Perus-Viljo NPK 8-5-1 on the fertilization level 80 kg N/ha yielded 22.6% by weight higher annual rye grass crop compared with that of the mineral fertilizer NPK 17-2-9, even on such a low soil organic carbon content as 0.7% by weight (only Perus-Viljo is now on the linear PEC vs pC/mC range, cf. Table 4).

Example 6

Accelerator for Biogas Production

To test a fertilizer composition of this invention as accelerator for biogas production a homogeneous mixture with the following composition was prepared: 85.5% by weight of used industrial silicate clay filter bed from fat filtering, 11% by weight of meat and bone meal, 2% by weight of ferrous sulphate, 1% by weight of sodium gluconate and 0.5% by weight of manganese sulphate, containing a total of 27.7% by weight priming carbon. This mixture was added 0.9% by weight into 1700 kg of sewage sludge in a continuous pilot biogas production reactor (total volume 4 $m^3$) during 19 days. The total methane production with the accelerator was high, 45 $m^3$ or 0.32 $m^3$/kg VS (volatile substance), compared with processing without the accelerator, 0.19 $m^3$/kg VS. The accelerated process was thus 70% more efficient compared with non-accelerated process.

As accelerator in the biogas production process the priming carbon content of the fertilizer of this invention is the minimum factor for the extra microbial growth and multiplying. Now nitrogen is needed only for the needs of the bacteria to grow and reproduce (plants are not involved), i.e. preferably as ammonium-nitrogen which is as such usable for bacteria. The amount of ammonium-nitrogen needed in this case was about 0.014% by weight and it was obtained straight from the sewage sludge, which contained it 0.2% by weight and total nitrogen 0.54% by weight. It is self evident that the two last demands of the claim 1 concerning the priming carbon, i.e. the C/N ratio and the proportion of total carbon, are not valid concerning this use because the fertilizer is not used as fertilizer but as rotting accelerator. In this example pC/$NH_4$—N ratio was 1.3:1, pC/N ratio was 0.46:1 and pC/VS ratio was 0.031:1 which are typical ratios when the fertilizer of this invention is used as accelerator in the biogas production processes.

Example 7

Accelerator for Composting

To test a fertilizer composition of this invention as accelerator for composting of rotted sewage sludge a homogeneous mixture with the following composition was prepared: 80% by weight of used industrial silicate clay filter bed from fat filtering, 10% by weight of meat and bone meal, 6.4% by weight of H4-5 peat, 2% by weight of ferrous sulphate, 1% by weight of sodium gluconate, 0.5% by weight of manganese sulphate and 0.1% by weight zinc sulphate, containing a total of 25.6% by weight priming carbon. This mixture (1.5 t, 1.0% by weight) was added to a mixture of rotted sewage sludge (120 t, 80% by weight) and field-dried H2-3 peat (30 t, 20% by weight), and the constituents were thoroughly mixed and shaped into a 250 $m^3$ pile (about 6 m*25 m*2 m). The pile was set up in the week 43 in 2012 and was left to stabilize for the coldest middle winter time. The pile was sampled and turned three times in three week periods, after which sampling was continued twice in four week periods.

The temperature in the pile did not increase much above 40 degrees Celsius due to its low energy content (the sludge had already been rotted in the bio gas production process) but the temperature stayed up for a long period being 25 degrees Celsius after three months from the start of the composting. The compost was stabilized in three months based on the decrease in its ability to produce carbon dioxide, which decreased from 8.3 (8 days from the start) through 4.8 (23 days from the start) to <2 mg $CO_2$—C/g VS/day (74 days from the start) (soil amendment compost is to be considered stabilized, when carbon dioxide carbon is produced <2 mg/g VS/day according to the Finnish decree for fertilizers 24/11, in its appendix I and in the national list of type names for fertilizers maintained by The Finnish Food Safety Authority Evira). After three months composting the nitrate-nitrogen concentration had started to increase giving a $NO_3$—N/$NH_4$—N ratio of 0.225 (compost is considered stabilized and mature when $NO_3$—N/$NH_4$—N>1). Usually the piles have been stabilized for six months without compost accelerator. Clearly the composting process has become accelerated and the produced soil amendment compost will be stabilized and mature within four months resulting in a possibility of more rapid circulation of the biodegradable wastes in the composting field. Thus the capacity of the composting field will increase and higher amounts of biodegradable wastes can be processed.

As accelerator in the composting process the priming carbon content of the fertilizer of this invention is the minimum factor for the extra microbial growth and multiplying. Now nitrogen is needed only for the needs of the bacteria to grow and reproduce (plants are not involved), i.e. preferably as ammonium-nitrogen which is as such usable for bacteria. The amount of ammonium-nitrogen needed in this case was about 0.013% by weight and it was obtained straight from the rotted sewage sludge, which contained it about 0.1% by weight and total nitrogen about 1% by weight. It is self-evident that the two last demands of the claim 1 concerning the priming carbon, i.e. the pC/N ratio and its proportion of total carbon, are not valid concerning this use because the fertilizer is not used as fertilizer but as composting accelerator. In this example pC/N ratio was 0.38 and pC/VS ratio was 0.014, which are typical ratios when the fertilizer of this invention is used as accelerator in the composting processes.

The invention claimed is:

1. A fertilizer composition, comprising
   a. a priming carbon (pC) source comprising at least 5% by weight of plant or animal derived fat or mono- or disaccharides or any mixture thereof; and
   b. a source of nitrogen,
   wherein the pC/N ratio of the fertilizer composition is from 7:1 to 2:1.

2. The fertilizer composition according to claim 1, wherein the priming carbon forms at least 33% by weight of the total carbon of the fertilizer composition.

3. The fertilizer composition according to claim 1, wherein the amount of carbon in said carbon source is from 2 to 35% by weight calculated from dry weight of the fertilizer composition.

4. The fertilizer composition according to claim 1, wherein amount of nitrogen in said nitrogen source is from 2 to 8% by weight calculated from dry weight of the fertilizer composition.

5. The fertilizer composition according to claim 1, wherein said carbon source is agricultural or industrial side product.

6. The fertilizer composition according to claim 1, wherein said nitrogen source is:
   a. an organic nitrogen source; or
   b. ammonium nitrogen source; or
   c. a mixture of (a) and (b).

7. The fertilizer composition according to claim 1, wherein it further comprises at least one member selected from the group consisting of:
   a. phosphorus source;
   b. a secondary nutrient source;
   c. a micronutrient source;
   d. potassium source; and
   e. a silicate source, wherein silicate fraction is 10 to 60% by weight calculated from dry weight of the fertilizer composition.

8. The fertilizer composition according to claim 7, wherein amount of soluble phosphorus is less than 0.5% by weight calculated from dry weight of the fertilizer composition.

9. The fertilizer composition according to claim 7, wherein said phosphorus source is selected from the group consisting of:
   a. an organic phosphorus source;
   b. a mineral phosphorus source; and
   c. a mixture of (a) and (b),
   and amount of phosphorus source is from 0.5 to 3% by weight calculated from dry weight of the fertilizer composition.

10. The fertilizer composition according to claim 7, wherein the silicate fraction comprises used industrial silicate clay filtering bed from fat filtering, calcium silicate, silicate mineral or a mixture thereof.

11. A method to feed soil bacteria and fertilize plants' said method comprising applying the fertilizer composition of claim 1 to soil.

12. A method to promote biodegradation of thatch in lawns, said method comprising applying the fertilizer composition of claim 1 to said lawns.

13. The method for manufacturing a fertilizer composition comprising the steps of:
   a. providing a priming carbon (pC) source and a nitrogen source, or a priming carbon (pC) source, a nitrogen source, silica and one or more other nutrients, wherein the priming carbon (pC) source comprises at least 5% by weight of planet or animal derived fat or mono- or disaccharides or any mixture thereof; and
   b. forming a mixture of the components such that the fertilizer composition has a pC/N ratio from 7:1 to 2:1.

14. The method of claim 13 further comprising a step forming the mixture of step b) into granulated or powdered fertilizer product.

15. the method of claim 13, wherein said carbon source or said nitrogen source is industrial or agricultural by-product and is provided in amount calculated based on actual carbon or nitrogen content of said source.

16. The method of claim 13, wherein the mixture of step b) is dried to decrease its water content.

* * * * *